United States Patent [19]

Törnblom

[11] Patent Number: 4,661,777

[45] Date of Patent: Apr. 28, 1987

[54] PLURAL FREQUENCY EDDY CURRENT METHOD AND APPARATUS WITH LIFT-OFF COMPENSATION FOR DETECTING FAULTS IN ELECTRICALLY CONDUCTIVE OBJECTS

[75] Inventor: Bengt H. Törnblom, Västerås, Sweden

[73] Assignee: Törnbloms Kvalitetskontroll AB, Västeras, Sweden

[21] Appl. No.: 699,594

[22] Filed: Feb. 8, 1985

[30] Foreign Application Priority Data

Feb. 10, 1984 [SE] Sweden .............................. 8400698

[51] Int. Cl.$^4$ ..................... G01N 27/90; G01R 33/12
[52] U.S. Cl. ..................................... 324/225; 324/232
[58] Field of Search ................ 324/225, 227, 232, 233

[56] References Cited

U.S. PATENT DOCUMENTS

| | | | |
|---|---|---|---|
| 3,197,693 | 7/1965 | Libby | 324/225 |
| 3,358,225 | 12/1967 | Peugeot | 324/225 |
| 3,974,442 | 8/1976 | Savidge et al. | 324/225 |
| 4,191,922 | 3/1980 | Harris et al. | 324/225 |
| 4,303,885 | 12/1981 | Davis et al. | 324/325 X |

FOREIGN PATENT DOCUMENTS

| | | |
|---|---|---|
| 7507857-6 | 7/1975 | Sweden . |
| 7613708-2 | 12/1976 | Sweden . |
| 2041535 | 9/1980 | United Kingdom ................ 324/225 |

*Primary Examiner*—Gerard R. Strecker
*Attorney, Agent, or Firm*—Watson Cole Grindle & Watson

[57] ABSTRACT

In the testing of electrically conductive test objects for the presence of flaws and the like using a transducer to generate electrical currents in the test object and to inductively sense such currents, drive signals of at least two different frequencies are use for the transducer and the different frequency component induced signals picked up by the transducer are processed in such ways that a testing process is obtained that has low LO (lift-off) dependence. The characterizing feature of the invention is that the signal processing is undertaken as a function of at least one variable which may be the lift-off distance.

11 Claims, 3 Drawing Figures

PLURAL FREQUENCY EDDY CURRENT METHOD AND APPARATUS WITH LIFT-OFF COMPENSATION FOR DETECTING FAULTS IN ELECTRICALLY CONDUCTIVE OBJECTS

TECHNICAL FIELD

The present invention is primarily related to the field of eddy current testing and is particularly concerned with testing for "localised changes" (as hereinafter defined) in a test object.

BRIEF DESCRIPTION OF PRIOR ART

A problem in connection with fault detection using, for example, an eddy current technique is the distance dependence (the so-called lift-off (LO) dependence) between the transducer and the object to be tested. LO dependence can give rise to considerable disturbance during testing and, therefore, conceals a real fault signal originating from, for example, a surface crack.

One method of suppressing the LO dependence is disclosed in Swedish Patent Applications No. 7507857-6, and 7613708-2. A similar method is described by Hugo L. Libby in "Introduction to Electromagnetic Nondestructive Test Methods" published in 1979 by Robert E. Kriger Publishing Co. (New York). A modification of the method of Libby is disclosed in the specification of U.S. Pat. No. 4,303,885.

All of the above-noted known methods of reducing LO dependence are based on the use of at least two carrier frequencies and on combining the information received from the respective frequency for suppressing undesired signals or variables.

A limiting factor in the above-noted known methods and indeed other known methods of reducing LO dependence is the fact that they are only really effective for measurements close to the object being tested (i.e. within a very limited LO region).

OBJECTS OF THE INVENTION

One object of this invention is to provide a solution to the above-mentioned problems and other problems associated therewith. A further object is to provide an optimizing method, which is capable, for example, of supplementing and improving the prior art fault-detecting methods mentioned above.

SUMMARY OF THE INVENTION

The present invention may, for example, be described as follows:

A device, which is primarily intended for testing and/or measurement of localised changes in/on electrically conductive test objects, comprises at least one transducer, which is fed with electrical signals, for example current of different frequency contents, so that currents, for example eddy currents, of corresponding frequency contents are induced in/on the test object. In this way, the electrical impedance of the transducer is influenced by the test object, via the inductive coupling between the transducer and the test object. As a consequence thereof, at least two signals or complexes of signals of completely or partially different frequency origin, directly or indirectly emanating from the transducer, can be signal processed, for example weighted and combined in such a way that the result, as a function of the distance of the transducer in relation to the test object, is constant within a limited operating range, when the test object displays no localised change at or adjacent the transducer, and different from the corresponding result in the case where there is a localised change in/on the test object.

Thus far, the description does not deviate from the prior art devices previously mentioned.

As the next stage in describing the novel features in the present invention, it is convenient, with reference to FIG. 1 of the accompanying drawings to introduce a somewhat different definition of the LO dependence than that previously used. Previously, the distance between the transducer and the actual surface of the test object has been designated the LO-distance.

Since the need to work with frequencies spanning a greater frequency range shows a tendency to increase with time, this fact also justifies a more exact definition of the LO-distance. This new concept of the LO-distance is of great and fundamental importance for an understanding of the present invention.

Some definitions which are important to an understanding of the invention, will now be introduced:

Included in the term TRANSDUCER is a device having a magnetic flux-generating part and a magnetic flux-sensing part consisting of at least one coil or wire loop, or the like. In principle, a coil fed with current may be both flux-generating, via the number of ampere turns, and flux-sensing, via the coil impedance. The transducer may also advantageously consist of a primary coil supplied with current and a sensing secondary coil in which an e.m.f. is induced. This e.m.f. then also contains information about disturbances in the eddy current propagation, and so on.

Included in the term TEST OBJECT is a billet, a sheet, a tube, a wire and a rod (irrespective of its cross-sectional profile).

Included in the term LOCALIZED CHANGE is meant, a metallurgical defect, a crack, a pore, a flake or a hole.

Included in the term DIFFERENCE is the difference between $H_1$ and $L_2$ in the accompanying FIG. 2. However, DIFFERENCE also relates to the quotient, that is, the relationship between, for example, $H_1$ and $L_2$ in FIG. 2.

The term FREQUENCY usually means the frequency or frequency component of the signals which the transducer is supplied with (in certain cases also designated carrier frequency, since often the changes to be detected are "superposed" on a carrier frequency). The term FREQUENCY may thus also include a complex of frequencies By the term LIFT-OFF (LO) is normally meant the distance between the transducer and the test object.

More specifically, in the present case the LO-distance is the distance between the transducer and the "sum current" (shortly to be described) of the respective frequency.

By the term TRANSFORMATION is meant, for example, vector transformation including variants thereof, such as described, for example, by Libby in U.S. Pat. No. 4,303,885, in Swedish Patent No. 7507857-6, and in Swedish Patent Application No. 7613708-2. An example of TRANSFORMATION is that signals, of completely or partially different frequency origins, are weighted and combined in such a way that the result permits or exhibits suppression of at least one undesired signal or variable (e.g. LO-dependence).

By the term WEIGHTING is meant, for example, the constants (representing e.g. potentiometer settings for setting amplifications) which are used in the transformation process. These constants often include the choice of plus or minus, where appropriate.

By the term RELATIVE LO-DISTANCE is meant, for example, the distance from a reference point, which is often the distance where the transducer signals have been balanced out instantaneously, that is, a type of starting point for the measurement which in certain cases is simpler to operate with than the ABSOLUTE LO-DISTANCE, which is the same as the real LO-distance.

The letter H is used to represent a high frequency or a signal derived from or dominated by a high frequency/carrier frequency.

The letter L is used to represent a low frequency or a signal derived from or dominated by a low frequency/carrier frequency.

BRIEF DESCRIPTION OF DRAWINGS

The invention will now be further described, by way of example, with reference to the accompanying drawings, in which.

BASIC PRINCIPLES OF OPERATION

Figure 1:
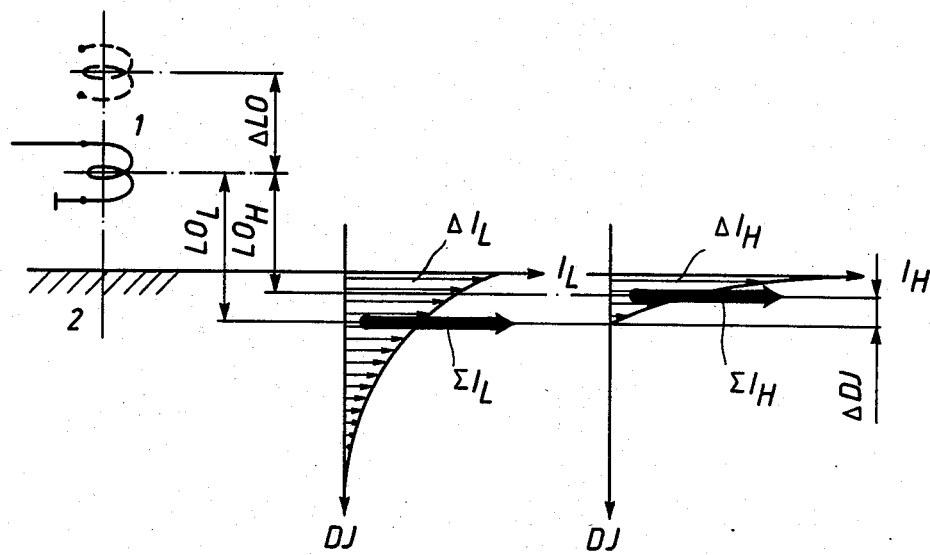
FIG. 1 represents the principle behind the measuring method of a device according to the invention showing the generation of H and L sum currents.

FIG. 1 shows a transducer 1 above the surface of an electrically conductive test object 2. The transducer is here supplied, as an example, with current, the frequency contents of which consist of a high frequency (H) and a low frequency (L). Via the flux induced/generated by the transducer 1, partial currents ($\Delta I_H$ and $\Delta I_L$) of corresponding high and low frequency contents are then induced in the test object 2. The magnitude of these currents are indicated on the righthand side in FIG. 1, and as will be clear the respective current intensities $I_L$ and $I_H$ are reduced as a function of the depth (DJ) below the surface of the test object. Now, if it is assumed that all the partial currents at each respective frequency are replaced by an imaginary sum current (shown as $\Sigma I_L$ and $\Sigma I_H$) for the respective frequency, these sum currents will be located at different depths below the surface. The difference in these sum current depths is designated $\Delta DJ$ in FIG. 1.

The two sum currents will then influence the transducer 1 in a manner corresponding to the sum of the partial currents, or better, in a manner corresponding to the total effect of all the partial currents. Since this influence is also a function of the distance between the respective sum current and the transducer, a new definition of the LO-distance can be considered, this being the distance between the transducer and the sum current of the respective frequency. In those cases where the transducer has a large propagation, it is possible, for example, in the same manner as for the partial currents, to introduce a fictitious "centre of gravity" for the transducer to which the LO-distance refers, and this has been done in FIG. 1. This means that the LO-distance will be different for different frequencies, for example $LO_H$ and $LO_L$, respectively, in FIG. 1, where $LO_L > LO_H$.

Figure 2:
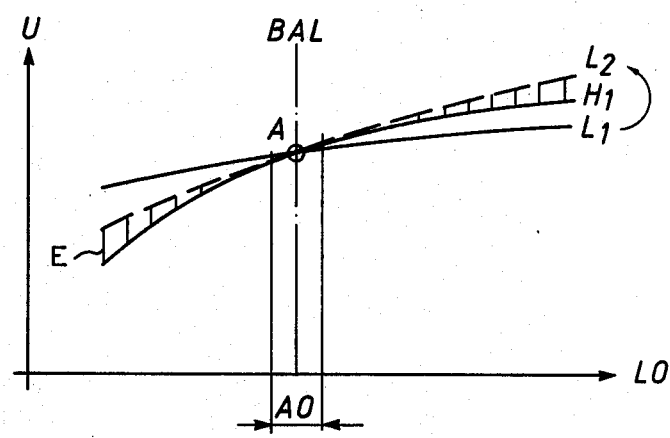
FIG. 2 shows the relationship between H and L signals for varying degrees or lift off.

The coupling between the transducer and the respective sum current can be described with the aid of complicated mathematical calculations. It is not necessary to consider these in detail here, but it is possible to employ a greatly simplified approach which nevertheless is sufficiently accurate to indicate an important fundamental effect, and to explain the advantages, of the present invention. For the simplified approach let it be assumed that the relationship between the transducer and the respective sum current is a simple inverted function of the LO-distance. Since $LO_L > LO_H$, it follows that the coupling between the transducer 1 and the test object 2 is different for the two different frequencies. This difference in the degree of coupling is the basic reason why signals of the different frequencies will follow different (non-coinciding) functions in the case of a varying LO-distance, these differences giving rise to a reduced accuracy of measurement (and all the resultant limitations this implies). This is illustrated in FIG. 2 where $H_1$ and $L_1$ represent signals of different frequency origins, emanating from the transducer, as a function of the LO-distance.

Especially when the relationship between LO and ADJ is small, that is, when the transducer 1 is located near the test object 2, the effect of the different depths of penetration will become more apparent.

From FIG. 1 it is also clear that when the transducer 1 is displaced from the position shown in unbroken line to the position shown in broken line, the LO-distance is changed for both frequencies by $\Delta LO$, which of course contributes to make the $H_1$ and $L_1$-functions separate from each other, with the exception of any crossing points (due to, e.g. balancing processes, etc.). By transforming/displacing $L_1$ to $L_2$ by means of, for example, a change of the amplification (of the low frequency), the difference (E) between $H_1$ and $L_2$ can be made small within a limited operating range (AO). In other words, within the range AO it is possible, with relative efficiency, to suppress the LO-dependence. This applies to the majority of known devices based on multi-frequency techniques.

From the specification of Swedish Patent Application No. 8302738-3, it is clear that it may be advantageous to operate with frequencies (i.e. carrier frequencies) which differ to a relatively large extent from each other (e.g. H/L>10). A consequence of this is, of course, that the difference (E) between current functions is amplified, whereby the operating range (AO) is reduced, which is a considerable limitation in practice. The present invention aims at extending the operating range by reducing the error in measurement (E). This reduction of measurement error is obtained by making the signal processing (e.g. the vector transformation or the weighting necessitated thereby) a function also of the absolute or relative LO-distance. A simple variant of this may then be for the transformation of $L_1$ to the new position $L_2$ to be performed dynamically, that is, so that $L_1$ is transformed to a differing extent depending on the LO-distance in question. In FIG. 2 this means that $L_1$ is transformed to such an extent that $L_2$ and $H_1$ have the same differential coefficient at the LO-distance in question (i.e. the two curves have the same inclination within the operating range).

Since the LO-distance is likely to vary continuously in practice, the transformation must conform thereto, that is, vary as a function of the LO-distance. In other words a dynamic (e.g. continuous) transformation/displacement of one or more vectors must be used. Known devices utilize, for example, fixed potentiometer settings during the transformation, which may then be considered a static transformation. This static transformation then relates to the "small signal parameters" which apply around a certain limited LO-distance. Examples of such known devices are those described by Libby and, for example, those described in the specification of U.S. Pat. No. 4,303,885. The specification of Swedish Patent No. 7507857-6, and Swedish Application No. 7613708-2 contain examples of static transformation by means of a so-called normalization process, which is to be regarded as a variant of transformation.

In practice, it may be sufficient to balance out the signals (instantaneously or continuously) coming from the transducer. An example of such balancing/compensating is described in the specification of Swedish Patent Application No. 7813344-4, which means that the functions $H_1$, $L_1$ and $L_2$ in FIG. 2 also may include control functions of this kind. For example, point A may be a balancing point which refers to a certain LO-distance (BAL) where the transducer signals have cancelled each other.

A consequence of the extended LO operating range is that the coupling between the transducer and the test object can now vary more sharply than what was previously the case. This means that the localised changes which are to be detected are detected with a greatly varying strength, depending on the LO-distance existing for the moment. This makes it very difficult to achieve a good signal-to-noise ratio (S/N) in the measurement.

As an example, a small oscillation mark (oscm) on a test object in the case of a small LO-distance—may give rise to a fault signal of the same amplitude as a large crack at a large LO-distance, thus deteriorating the S/N ratio. To remedy this, the amplification and/or the reference level can be controlled by the absolute or relative LO-distance. This means that the amplification of the fault signal, or the reference level (threshold level) with which the fault signal is compared, is a function of the LO-distance. One further advantage of this method is that the variation in amplification, which is often caused by the dynamic transformation, can be eliminated in a relatively simple manner.

An important detail in certain applications of the invention is how the LO-distance should be measured. An elegant way of doing this, is to use the same transducer for the LO-measurement as is used for detecting a localised change in the test object. However, this does not exclude the possibility of using a separate transducer for the LO-measurement, which may be justified in certain cases. To this end, it may be necessary to use a technique other than eddy current measurement. For example, when detecting cracks on hot billets, temperature variations on the surface of the billet may disturb the eddy current measurement of the LO-distance, and therefore the LO-measurement may take place by means of a separate transducer utilizing, for example, compressed air, IR detector, limit positions, etc.

Swedish Patent No. 7507857-6 mentions weighting and linearization. However, in this case it is a question of conventional technique, that is, static principles which are not a function of any variable. Nor do these prior art weighting processes enable the extension of the operating range, which is made possible by the present invention.

DESCRIPTION OF PREFERRED EMBODIMENT OF DEVICE

Figure 3:
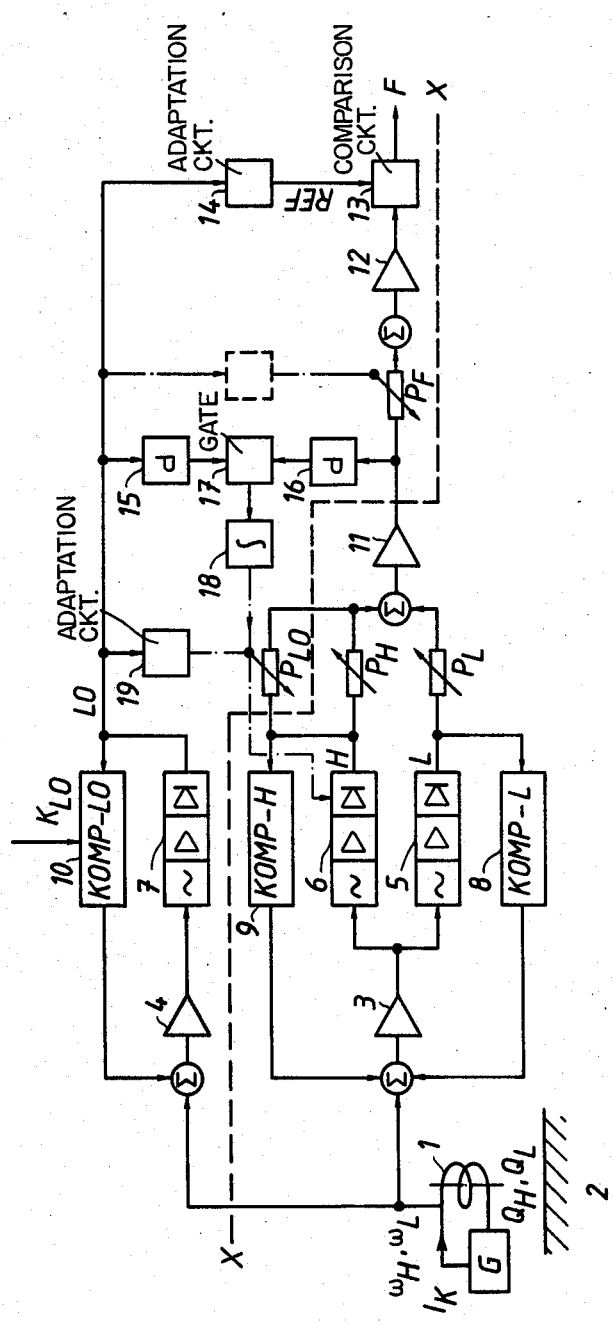
FIG. 3 shows a circuit diagram for a device according to the invention, the inventive feature being that shown above the chain line X—X in FIG. 3.

FIG. 3 shows one of many feasible embodiments of the present invention, which will be described in the following.

The transducer 1 is supplied from a current or voltage generator G with an electrical current $I_K$, containing respective high and low frequency components $\omega_H$ and $\omega_L$ which generate fluxes $\phi_H$ and $\phi_L$ which, via the transducer, interact with the test object 2. Across the transducer, which is located near the test object, a signal, for example a voltage, is generated which is proportional to the electric impedance of the transducer. This transducer voltage is fed to two amplifiers 3 and 4, via the indicated summational points $\Sigma$. After the signal has been amplified in amplifier 3, $\omega_H$ and $\omega_L$ are separated in one high 6 and one low 5 frequency channel, each of which contains a filter, an amplifier and a phase-controlled rectifier, the output signals of which channels are respectively marked H and L, in FIG. 3. The output signals H and L feed respective balancing servos 9 and 8 which, for example, continuously balance/compensate the high and low frequencies or frequency components of the transducer output signal. Of course, the number of frequencies can be increased if this is suitable with regard to the application in question. The H- and L-signals also feed an amplifier 11, via potentiometers $P_H$ and $P_L$. These potentiometers can be regarded as weighting potentiometers, that is they represent constants in the transformation process.

Part of the novel idea of the invention can be seen to reside in the fact that these "constants" will be varied as a function of some variable; thus, they will, other than instantaneously, no longer be pure constants. If H and L are chosen with different polarities, the H- and L-signals may largely balance each other out in the case of a varying LO-distance, if the $P_H$ and $P_L$ settings are appropriately chosen and the LO operating range (AO) is limited, provided the test object 2 does not exhibit any changes adjacent to or in the transducer 1. The consequence of this is that the output signal from the amplifier 11 approaches zero, that is, the LO-dependence is suppressed. As will be clear from the reasoning and particularly from FIG. 2, the measuring principle thus far is based on a so-called small signal parameter method. However, in the case of a larger LO operating range, a larger output signal will appear on the output of the amplifier 11 and which is to be regarded as a disturbance. The reason for this is, of course, that the region, within which the small signal process can be considered to apply, has now been exceeded.

Thus far, the portion of FIG. 3 located below the dashed line has been described. This portion can be considered the conventional and known portion of FIG. 3, that is, the "small signal portion".

The novel feature of FIG. 3 will now be described, which involves giving the small signal process a dynamic dimension which significantly extends the operating range, for example, with substantially retained performance.

In addition to feeding the amplifier 3, the transducer signal also feeds integers 4, 7 and 10 which are largely built up as the conventional H-channel.

The difference resides in the fact that the control circuit, integer 10, can be activated and interrupted via a $K_{LO}$-input. By activating the circuit 10 instantaneously when the transducer is located, for example, in a certain position relative to the test object and then locking the servo, the output of the phase-controlled rectifier of channel 7 will assume a signal level which, thereafter, is a function of the LO-distance of the transducer from the test object; in other words, the LO-vector of the transducer is measured in this way. This signal is indicated by LO in FIG. 3 and as will now be described it constitutes an important control signal.

If the potentiometers $P_H$ and $P_L$ are regarded as preselected coarse settings, it is simple to achieve a fine setting by, for example, series- or parallel-connecting one or more extra potentiometers thereto. Therefore, in FIG. 3 a more highly ohmic potentiometer $P_{LO}$ has been connected, which may be regarded as a fine or correction potentiometer. As a simpler variant, this potentiometer ($P_{LO}$) can be set continuously via an adaptation unit 19, the input signal to which consists of the LO-signal. This means that the transformation is automatically self-adjusting (adaptive) as a function of the absolute or relative LO-distance, whereby the error in measurement (E in FIG. 2) is minimized.

In principle, this adaptive function can also be based on other variables than the LO-distance, which makes the method described of very general applicability. As an alternative to setting the potentiometer $P_{LO}$ via the unit 19, the potentiometer $P_{LO}$ can also be set in a more sophisticated manner via an integrator 18 connected to integers 15, 16 and 17. This method relies on determining the differentrial coefficient (or sign only) of the LO-signal in a differentiating unit 15, which means that also the direction of any change in the LO-signal is sensed, that is if the LO-distance increases or decreases. At the same time, differentiating unit 16 senses the differential coefficient of the output signal from the amplifier 11, that is, if the error in measurement increases or decreases. The output signal from the unit 16 feeds the integrator 18, via a gate circuit 17, which may consist of a simple contact function controlled by the unit 15. If a suitable time constant for the integrator 18 is chosen, the setting of the potentiometer $P_{LO}$ can thus be automatically adjusted to make it substantially independent of any drifts, or the like in the LO-measurement. In this connection it is important to note that this more sophisticated method of setting also involves an adaptive adaptation to the surface structure of the test object, for example so that unimportant surface irregularities (such as, for example oscillation marks), can be suppressed in a better way.

If required, the unit 19 may include function transforming circuits for obtaining an optimum control function, that is, the function that the potentiometer $P_{LO}$ is to follow.

Since the output signal from the amplifier 11 may also include, in addition to the error in measurement, information as to any changes in the test object, the time constant of the integrator 18 should be chosen with this in mind. The diffentiating units 15 and 16, may in certain cases be omitted if, for example, the balancing servos 8 and 9, operate continuously and rapidly, which then results in a differentiating effect corresponding to that of the diffentiating units 15 and 16. In certain cases it is only necessary to use the units 15 and 16 as sign sensors or to use them to sense just the magnitude of the differential co-efficient.

In the same way as the potentiometer $P_{LO}$ can be controlled by the LO-signal via the units 18 and 19, the phase-controlled rectifiers in the channels can also be controlled from these. An example of this is shown in FIG. 3 where phase control of channel 6 can be controlled—for example fine-adjusted—directly or indirectly by the LO-signal. This means that one or more of the vectors which are included in the transformation process can be varied both in magnitude and direction as a function of a variable, such as the LO-distance.

The signal obtained from the amplifier 11 is amplified (positively or negatively) in a further amplifier 12, the amplification being determined by the value of a potentiometer $P_F$. As will be clear from FIG. 3, this setting can also be controlled directly or indirectly by the LO-signal. The signal from integer 12 is then passed to a comparison circuit 13, which may, for example, consist of a comparator whose second input (REF) is fed via an adaptation circuit 14 influenced by the LO-signal. The output signal (F) from the unit 13 therefore indicates, with substantially constant sensitivity, when a change of a certain magnitude occurs in the test object, this indication being, within reasonable limits, independent of the LO-distance.

During, for example, crack detection on hot billets or slabs, the transducer is moved rapidly across the surface of the billet by means of, for example, an industrial robot. Because of oscillation marks and other irregularities in/on the billet surface, the distance between the transducer and the test object, due to the relative movement between the transducer and the billet surface, will vary rapidly and greatly in an irregular manner. This makes it very difficult—perhaps impossible—to achieve a sufficient accuracy of measurement on uneven surfaces using pure static transformation and amplification. The basic reason for this is that the sum currents for different frequencies have different coupling to the transducer, which in turn is caused by the different distances to the transducer.

According to a different example, the second differential coefficients for the coefficients of coupling of the respective frequencies between the transducer and the test-object differ from each other, whereby a static transformation is only ideal at the LO-distance to which the transformation setting refers. In this case, of course, the term transformation refers to the whole transformation process, including the associated suppression of undesired signals (via e.g. summation, etc.). By continuously and automatically correcting the transformation process as well as the amplification of the fault signal starting from the current distance (existing for the moment) between the transducer and the test object, the transformation can be optimised over a larger LO-distance; in other words: a dynamic transformation process is employed. Since the invention in its more complex application comprises a combination of a dynamic transformation process, with the associated suppression of undesired signals, and dynamic amplification adjustment, this in included in the expression "signal processing".

Swedish Patent No. 7507857-6 describes a device which only needs two signals originating from two different frequencies to suppress the LO-dependence. These signals are weighted against each other via the so-called normalization. In this simple case, the transformation according to the present invention only means that, for example, the setting of the normalization is adjusted dynamically.

Finally an important observation. The present invention also covers methods and devices in which the influence of the transducer on the test object is measured via indirect methods, that is to say that changes in the transducer impedance, etc., are measured in the form of, for example, frequency changes directly or indirectly independently of the electrical impedance of the transducer. An example of such a device is the case where the transducer is part of a self-oscillating oscillator and where the changes in the transducer impedance are then directly transformed into frequency changes in the oscillator frequency which are then easily detected and transformed.

The present invention can also be considered to define a method of successively or continuously adaptively optimizing the signal processing, including the transformation function, with respect to one or more variables, in which case the invention can be seen to describe a general method. Of course, the invention can advantageously be implemented by means of a computer and associated electronic adaptation equipment, which is within the scope of the invention. The accompanying drawings only show the principle and have not been drawn to scale. The present invention can be varied in many ways within the scope of the appended claims.

The foregoing description should therefore be regarded as an example of the principle of implementing the invention.

What is claimed is:

1. A device for testing an electrically conductive object for the presence of a localized change therein, comprising:
   at least one transducer adapted to be moved over the surface of said object at a given lift-off distance therefrom;
   means for feeding said at least one transducer with electrical signals having at least two different frequencies to induce electrical currents in the object;
   said transducer sensing said electrical currents and providing a transducer output signal representative thereof and having components representing said at least two different frequencies; and
   means for processing said transducer output signal to provide an output signal unaffected by a change in said lift-off distance and representative of a localized change in the object in the vicinity of said at least one transducer, and including first circuit means for processing the components of said transducer output signal to generate said output signal, said first circuit means having an adjustable element for adjusting said output signal and further including second circuit means for processing a selected one of said components of said transducer output signal and connected to said first circuit means for adjusting said adjustable element to compensate said output signal for changes in said lift-off distance.

2. The device according to claim 1 in which said processing means further includes at least one control circuit for actuating said second circuit means when said at least one transducer assumes a certain lift-off distance.

3. The device according to claim 2 wherein said at least one control circuit also measures said lift-off distance.

4. A device according to claim 1, further comprising means to generate a signal proportional to the differential coefficient of said lift-off distance, said proportional signal automatically actuating said second circuit means.

5. A device according to claim 1, wherein said second circuit means automatically changes, and a function of said lift-off distance, the magnitude of said output signal originating from a localized change in said object.

6. A device according to claim 1, wherein said second circuit means includes means for comparing the output signal originating from a localized change in said object with reference information which is a function of said lift-off distance.

7. A device according to claim 1, in which said second circuit means includes means for providing an automatic fine adjusting superposed on a pre-set coarse setting of said lift-off distance.

8. A method for testing an electrically conductive object of the presence of a localized change therein, comprising:
   moving at least one transducer over the surface of said object at a predetermined lift-off distance therefrom;
   exciting said at least one transducer with electrical signals having at least two different frequencies to induce electrical currents in said object;
   sensing the electrical signals with said at least one transducer and providing a transducer output signal representative thereof and having components representing said at least two different frequencies; and
   processing said transducer output signal to provide an output signal unaffected by a change in lift-off distance and representative of a localized change in the object in the vicinity of said at least one transducer, said processing including obtaining a selected one of said components of said transducer output signal and adjusting the transducer output signal in response to said obtained selected one of said components to compensate said output signal for changes in said lift-off distance.

9. The method according to claim 8 wherein the adjusting of the said transducer output signal takes place when said at least one transducer assumes a certain lift-off distance.

10. The method according to claim 8 wherein said step of processing includes generating a signal proportional to the differential coefficient of the distance between said object and said at least one transducer and automatically adjusting the signal output in accordance with said differential coefficient.

11. The method according to claim 8 wherein said step of processing includes automatically changing the magnitude of a fault signal originating from a localized change in said object as a function of said lift-off distance.

* * * * *